United States Patent
Fung et al.

(10) Patent No.: US 7,361,908 B2
(45) Date of Patent: Apr. 22, 2008

(54) RADIATION DOSE ESTIMATION FOR RADIOCHROMIC FILMS BASED ON MEASUREMENTS AT MULTIPLE ABSORPTION PEAKS

(75) Inventors: Karl Ka Lok Fung, Hong Kong (CN); Kit Yee Lee, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 70 days.

(21) Appl. No.: 11/403,677

(22) Filed: Apr. 13, 2006

(65) Prior Publication Data
US 2007/0241289 A1    Oct. 18, 2007

(51) Int. Cl.
*G01N 21/00* (2006.01)
(52) U.S. Cl. .................................. 250/474.1
(58) Field of Classification Search ............. 250/474.1
See application file for complete search history.

(56) References Cited

U.S. PATENT DOCUMENTS

| | | | |
|---|---|---|---|
| 4,489,240 A * | 12/1984 | Kronenberg et al. ...... | 250/474.1 |
| 5,767,520 A * | 6/1998 | Donahue et al. ......... | 250/474.1 |
| 6,927,859 B2 | 8/2005 | Kwok et al. | |
| 2004/0008347 A1* | 1/2004 | Kwok et al. ................ | 356/331 |
| 2006/0017009 A1* | 1/2006 | Rink et al. ................ | 250/484.5 |

OTHER PUBLICATIONS

Lee K.Y., Fung K.L., and Kwok, C.S. (2004), "Development and initial evaluation of a spectral microdensitometer for analyzing radiochromic films". Physics in Medicine & Biology, vol. 49, pp. 5171-5183.
Lee K.Y., Fung K.K.L., and Kwok C.S. (2005), "Dual-peak dose measurement for radiochromic films by a newly developed spectral microdensitometer", Medical Physics, vol. 32, pp. 1485-1490.
Lee K.Y., Kwok C.S., Fung K.L. (2004), "Development of a microdensitometer system for reading radiochromic films", ESTRO 23, Amsterdam, The Netherlands, Oct. 24-28, 2004, S445.
Lee K.Y., Kwok C.S., Fung K.K.L. (2005), "A new method of reading radiochromic films with improved sensitivity", 8th Biennial ESTRA Meeting on Physics and Radiation Technology for Clinical Radiotherapy, Lisboa, Portugal, Sep. 24-29, 2005, S196.

(Continued)

*Primary Examiner*—David P. Porta
*Assistant Examiner*—Marcus H Taningco
(74) *Attorney, Agent, or Firm*—Evan Law Group LLC

(57) ABSTRACT

A method of estimating a radiation dose deposited on a radiochromic film based on absorption measurements at least at two wavelengths as well as devices implementing the estimation method. The method includes the following steps: (a) measuring absorption values at a first wavelength and a second wavelength; (b) converting the absorption values at the two wavelengths to dose values at the corresponding wavelengths by using a calibration procedure; (c) obtaining a weighting factor curve (weighting factor vs. dose) at each wavelengths; and (d) obtaining an estimate of irradiation dose at the location on the radiochromic film by minimizing the objective function which takes the weighting factors and the dose values at both wavelengths as input.

18 Claims, 4 Drawing Sheets

OTHER PUBLICATIONS

Lee K.Y., Fung K.K.L., and Kwok C.S. (2005), "Verification of a SRS treatment plan delivered by a 5-mm collimator using high-resolution radiochromic film dosimetry", 8th Biennial ESTRA Meeting on Physics and Radiation Technology for Clinical Radiotherapy, Lisboa, Portugal, Sep. 24-29, 2005, S193.

Lee K.Y., Fung K.K.L., and Kwok C.S. (2005), "Verification of a linac-based SRS treatment plan delivered by a 5-mm collimator", 13th Annual Scientific Meeting of the Hong Kong College of Radiologists, Hong Kong, Oct. 21-23, 2005, 118.

* cited by examiner

RADIATION DOSE ESTIMATION FOR RADIOCHROMIC FILMS BASED ON MEASUREMENTS AT MULTIPLE ABSORPTION PEAKS

BACKGROUND OF THE INVENTION

1. Field of the Invention

The invention relates to a method of estimating an irradiation dose imparted to patients receiving radiation treatment. Specifically, the invention relates a method of estimating an irradiation dose based on absorption measurements of a radiochromic film at two absorption wavelengths.

2. Description of the Related Art

Radiochromic films are increasingly used in medical dosimetry in assessing radiation doses imparted to patients receiving radiation treatment. Radiochromic films are transparent films which change from colorless to different shades of a bluish color upon irradiated by ionizing radiation. The degree of shading depends on the amount of energy deposited on the films. They are insensitive to daylight and are tissue equivalent; their responses are slightly energy dependent and practically dose-rate independent. They can offer a very fine resolution up to 1200 lines/mm due to their grainless nature. All these advantages render them a better two-dimensional dosimetry medium over the silver-halide type of radiographic film. Radiochromic films have been therefore found to be a valuable tool in high-resolution film dosimetry where steep dose gradients are encountered.

An exposed radiochromic film needs to be read out before any quantitative analysis of absorbed doses can be made.

With devices such as the microdensitometer disclosed in U.S. Pat. No. 6,927,859, which allows high-resolution read out of radiochromic films at any suitable wavelengths, it is now possible to obtain absorption data at any given wavelengths. It is known that the absorption spectrum of the radiochromic films has two distinct absorption peaks in the visible spectrum, the major peak at about 672 nm and the minor peak at about 610 nm. On the basis of this spectral information, one may realize that the measurement of the transmittance should be made at the major absorption peak to attain the maximum sensitivity of the dose response. However, the measurement may easily saturate at high doses due to the strong absorption at these levels. On the other hand, if the measurement is carried out at the wavelength of the minor peak, the measurement will not be sensitive enough to detect low doses. Thus, an estimation method relying on a single wavelength absorption data has its shortcomings.

SUMMARY OF THE INVENTION

In some embodiments of the present invention, there is provided a method of estimating a radiation dose at a location on a radiochromic film by combining absorption data at two or more wavelengths of the major and minor absorption peaks to extend the range of measurement and increase the accuracy and sensitivity thereof. Using two-wavelength based dose estimation for example, the method comprises: (a) measuring absorption values at a first wavelength and a second wavelength; (b) converting the absorption values at the two wavelengths to dose values at the corresponding wavelengths by using a calibration procedure; (c) obtaining a weighting factor curve (weighting factor vs. dose) at each wavelengths; (d) obtaining an estimate of irradiation dose at the location on the radiochromic film by minimizing the objective function which takes the weighting factors and the dose values at both wavelengths as input.

In other embodiments of the present invention, there is provided a device for estimating a radiation dose at a location on a radiochromic film, comprising a component for minimizing the following objective function:

$$OF(d) = \sqrt{\omega_{w1} \cdot (d_{w1} - d)^2 + \omega_{w2} \cdot (d_{w2} - d)^2},$$

wherein $\omega_{w1}$ and $\omega_{w2}$ are weighting factors at doses $d_{w1}$ and $d_{w2}$ for a first wavelength and a second wavelength, respectively; $d_{w1}$ and $d_{w2}$ are dose values converted from actual net absorption measurements at said first and second wavelength, respectively. The device may further include a component for measuring optical density of a radiochromic film at a given wavelength, a component for deriving a curve of weighting factor versus radiation dose, and/or a component for converting an optical density into dose value.

In still other embodiments of the present invention, there is provided a device for estimating a radiation dose at a location on a radiochromic film, comprising an implementation of one or more steps in the above described method, said implementation being realized in software, hardware or a combination of both so dose estimation of a radiochromic film may be partially or entirely obtained automatically once the device has read the film.

The Various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

REFERENCES

1. Lee K. Y., Fung K. L. and Kwok C. S. (2004). "Development and initial evaluation of a spectral microdensitometer for analysing radiochromic films". *Physics in Medicine & Biology*, 49: 5171-5183.
2. Lee K. Y., Fung K. K. L. and Kwok C. S. (2005). "Dual-peak dose measurement for radiochromic films by a newly developed spectral microdensitometer". *Medical Physics*, 32: 1485-1490.
3. Lee K. Y., Kwok C. S. and Fung K. L. (2004). "Development of a microdensitometer system for reading radiochromic films". ESTRO 23, Amsterdam, The Netherlands, 24-28 October: S445.
4. Lee K. Y., Kwok C. S. and Fung K. K. L. (2005). "A new method of reading radiochromic films with improved sensitivity". 8$^{th}$ Biennial ESTRO Meeting on Physics and Radiation Technology for Clinical Radiotherapy, Lisboa, Portugal, 24-29 September: S196.
5. Lee K. Y., Fung K. K. L. and Kwok C. S. (2005). "Verification of a SRS treatment plan delivered by a 5-mm collimator using high-resolution radiochromic film dosimetry". 8$^{th}$ Biennial ESTRO Meeting on Physics and Radiation Technology for Clinical Radiotherapy, Lisboa, Portugal, 24-29 September: S193.
6. Lee K. Y., Fung K. K. L. and Kwok C. S. (2005). "Verification of a linac-based SRS treatment plan delivered by a 5-mm collimator". 13$^{th}$ Annual Scientific Meeting of The Hong Kong College of Radiologists, Hong Kong, 21-23 October: 118.

DETAILED DESCRIPTION OF PARTICULAR EMBODIMENTS

Measuring Absorption Values at Multiple Wavelengths

Figure 1:
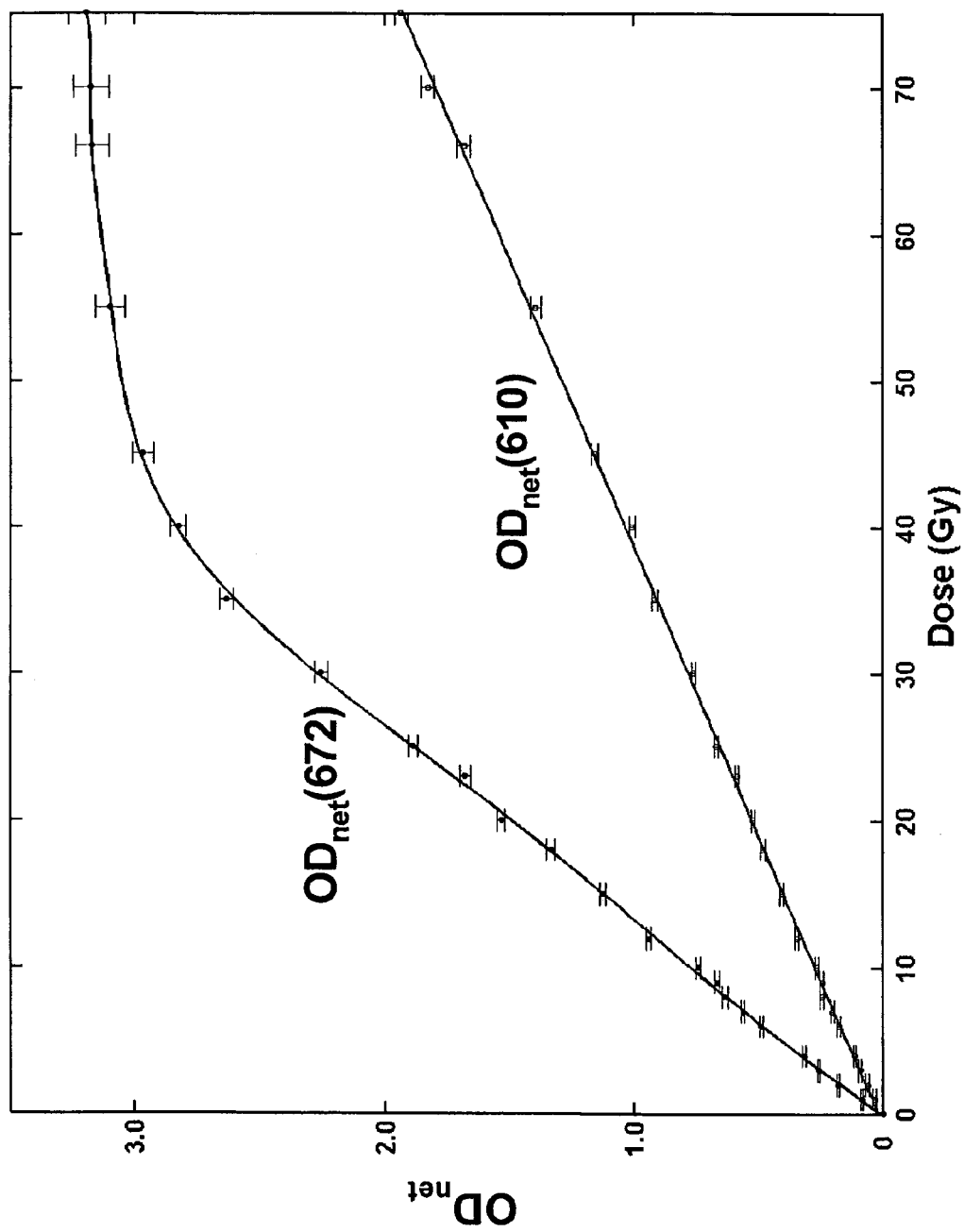
FIG. 1 shows film calibration curves at two wavelengths.

For a particular embodiment of the invention, the spectral microdensitometer disclosed in U.S. Pat. No. 6,927,859 may be employed to measuring the absorption value at a particular location of the radiochromic film (RCF) at one or more given wavelengths. The microdensitometer has a monochromator which provides an analyzing light of a given wavelength (which may be tunable), a film holder on a high-precision scanning stage, a transmission microscope coupled to a thermoelectrically cooled CCD camera, a microcomputer and corresponding user interfaces. As the wavelength of the analyzing light is tunable for the particular embodiment, it is possible to measure the absorption (or inversely transmittance) at the two absorption peaks with increased sensitivities. The high spatial resolution, on the order of micrometers, of the apparatus is achieved through the integration of the use of the microscope and a measure-and-step technique to cover the area of interest on a RCF. The content of U.S. Pat. No. 6,927,859 is incorporated herewith by reference in its entirety.

Although the above microdensitometer provides good results in practicing the present invention, other devices which can measure RCF's absorption/transmittance of an analyzing light at given wavelengths tuned to the absorption peaks of the RCF may also provide satisfactory results. In this disclosure, the terms "absorption value" and "optical density" are used interchangeably. Optical density (or absorption value) is an expression of the transmittance of an optical element at a given wavelength. Optical density is expressed by $\log_{10}(1/T)$ where T is transmittance.

Converting Absorption Value to Dose Value at a Given Wavelength

The measured absorption value at a particular location on a RCF reflects the radiation dose at the location but may not be in exact linear relationship. The absorption value therefore needs conversion to obtain the corresponding radiation dose. To perform the conversion, the dose response of the RCF as a function of dose and wavelength of the analyzing light has to be established first. An unexposed RCF is cut into small pieces of $2\times2$ cm$^2$. Careful handling the RCFs is recommended. Two film are in an envelope to serve as blank pieces. Other film pieces are exposed in a Solid Water™ (Gammex RMI, WI) phantom at 5 cm depth with a source-to surface distance of 100 cm using a 6 MV photon beam from a Varian 600 C/D Clinac® (Varian Medical Systems, Inc., Palo Alto, Calif.) under a full scattering condition. A uniform field of $25\times25$ cm$^2$ is used to deliver the dose to the film pieces. The output of the Clinac® has been calibrated according to an international dosimetry protocol and is traceable to a primary standard. The dose given ranges from 0.5 to 75 Gy, a typical range in the clinical setting. All exposed film pieces together with the blank pieces are kept in the same condition after irradiation. The film pieces are read 24 hours later for the coloration to stabilize. The measurements are taken in a darkened room to eliminate the effect of stray light on the transmittance values obtained.

The blank and exposed film pieces are then placed on a calibration film holder for readout. The measurement from the blank film piece is required for the determination of the net optical density ($OD_{net}$) for the exposed one. In order to lessen the effect of non-uniformity of the RCFs on the measurement obtained, 5 different locations on each film are measured. These locations are at the centre and 4 corners of an imaginary square of side 3 mm cast on the central part of the film piece. The measurement size is a square matrix of size $100\times100$ measuring $0.5\times0.5$ mm$^2$. Ten measurements are made at each location and the pixel values thus obtained are averaged and converted to give the $OD_{net}$ at that location. The final $OD_{net}$ reported for each film piece is the mean of the 5 $OD_{net}$s obtained at those designated locations. Readout is done first at 672 nm and then at 610 nm. A calibration curve of $OD_{net}$ as a function of known doses for each wavelength is then established using a polynomial curve fitting technique. Since there is a known batch-to-batch variation in the sensitivity of the RCF, the calibration curves established are valid only for this batch of films.

FIG. 1 shows the resulting calibration curves of $OD_{net}$ as a function of dose measured at 672 nm and 610 nm. As expected, the $OD_{net}$ curve has a strong dependence on the wavelength of the analyzing light used. The dose required to achieve an $OD_{net}$ of 1 ($DOD_{net}1$) for $OD_{net}(672)$ and $OD_{net}(610)$ curves are 13.2 Gy and 38.7 Gy respectively. This indicates that the RCF is about 3 times more sensitive if analyzed at 672 nm than at 610 nm. If compared to the white light and He—Ne densitometer on which the $DOD_{net}$ are 100 and 56 Gy respectively, the present design has a significant improvement in the dose response of the RCF even if it is measured at a wavelength of the minor absorption peak.

The $OD_{net}(672)$ curve has a straight line portion with a steep slope below 35 Gy and tends to level out with a slight slope beyond this dose level due to the strong absorbance at high doses. Also noted is the uncertainty of the $OD_{net}$ shown by the vertical error bars (±1 s.d. (standard deviation)) tends to be larger as the dose increases because smaller number of photons reach the CCD camera at these dose levels. On the other hand, the $OD_{net}(610)$ calibration curve is linear in the dose range up to a dose of 75 Gy. Beyond 35 Gy, the slope of $OD_{net}(610)$ is comparatively steeper than what is achieved by the $OD_{net}(672)$ curve.

It follows that, below 35 Gy, the RCF analyzed at a wavelength of 672 nm will be much more sensitive to a dose change than at 610 nm as indicated by the slopes of the curves. When the dose approaches 35 Gy, the sensitivity will shift to the measurement using the wavelength of the minor peak as the $OD_{net}(672)$ curve tends to level out and carries a larger uncertainty above this dose level. The measurement at 610 nm beyond 35 Gy extends the dynamic range of the dose measurement with a reasonable sensitivity otherwise not achievable with the wavelength of the major peak due to the high absorbance. Therefore, if one is given an option to choose the wavelength of the analyzing light according the dose magnitude, one can be assured that the measurement is always done at the maximum attainable sensitivity. Based on these ideas, the present invention provides a new calculation method (an algorithm) which takes as input measurements at multiple (at least two) wavelengths in order to extend the dynamic range of the dose measurement and at the same time to increase its sensitivity and accuracy.

Obtaining the Weighting Factor vs. Dose Curve

A measure of noise for the $OD_{net}$ value can be represented by the coefficient of variation (CoV=s.d./mean) of the $OD_{net}$ value. In other words, the uncertainty in the $OD_{net}$ value is related to the level of the noise associated, it is logical to derive the weighting factor from the CoV of $OD_{net}$ value with respect to the dose. In this sense, the more the noise an $OD_{net}$ is associated at a particular dose level, the smaller the weighting factor should be. Therefore, the formulation for the weighting factor used in the algorithm is proposed to be the reciprocal of the CoV and represented by $$\omega_{wavelength} = \frac{1}{CoV}.$$

Figure 3:
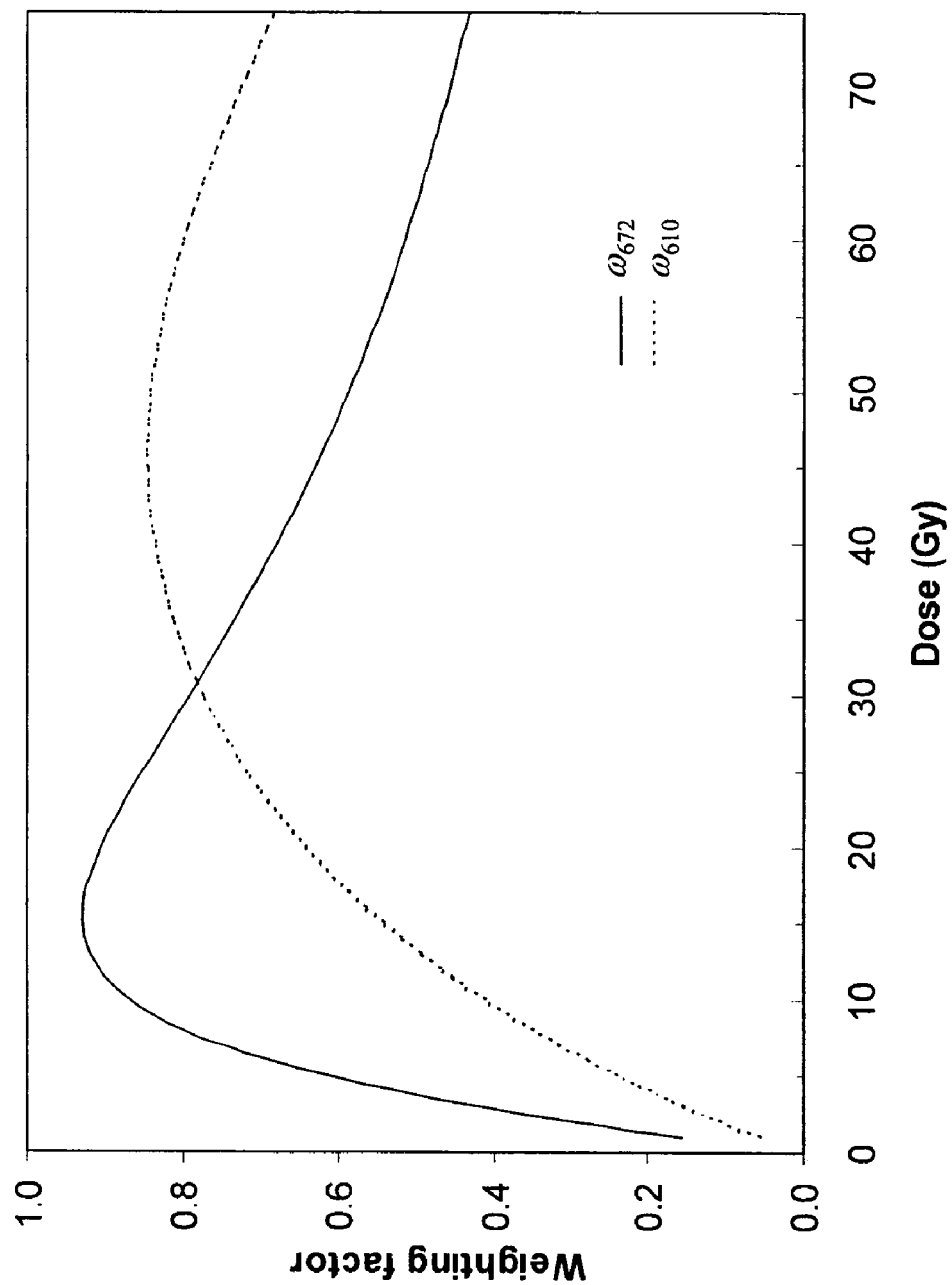
FIG. 3 shows curves of weighting factor verses dose.

The weighting factor for the specific wavelength actually depicts the level of significance of the $OD_{net}$ measurement with respect to its noise level at a particular dose when minimizing the objective function (OF). FIG. 3 shows the curves of the weighting factors for the wavelength of 672 nm and 610 nm in the dose range from 0.5 Gy to 75 Gy, which are derived by fitting the reciprocal of the CoVs of the $OD_{net}$s with respect to the corresponding dose levels. The CoV is obtained by repeating a measure for a sufficient number of times under the same conditions and calculating the standard deviation and the mean of the set of measurement. The CoV at a given dose and a given wavelength is the standard deviation divided by the mean. After a sufficient number of CoVs are obtained within a certain dose range, a weighting factor for a given wavelength in the dose range can be obtained by a fitting process. The fitted curves are then used to calculate the weighting factor for any dose value at the wavelength used. Since the curve of the weighting factor is primarily derived from the $OD_{net}$ measurement with respect to the dose, it may be valid only for this batch of films. A different batch may have different characteristics and in that case a new curve should be obtained based on actual measurements conducted on the particular batch.

Minimizing an Objective function to obtain a Best Dose Estimation

Figure 2:
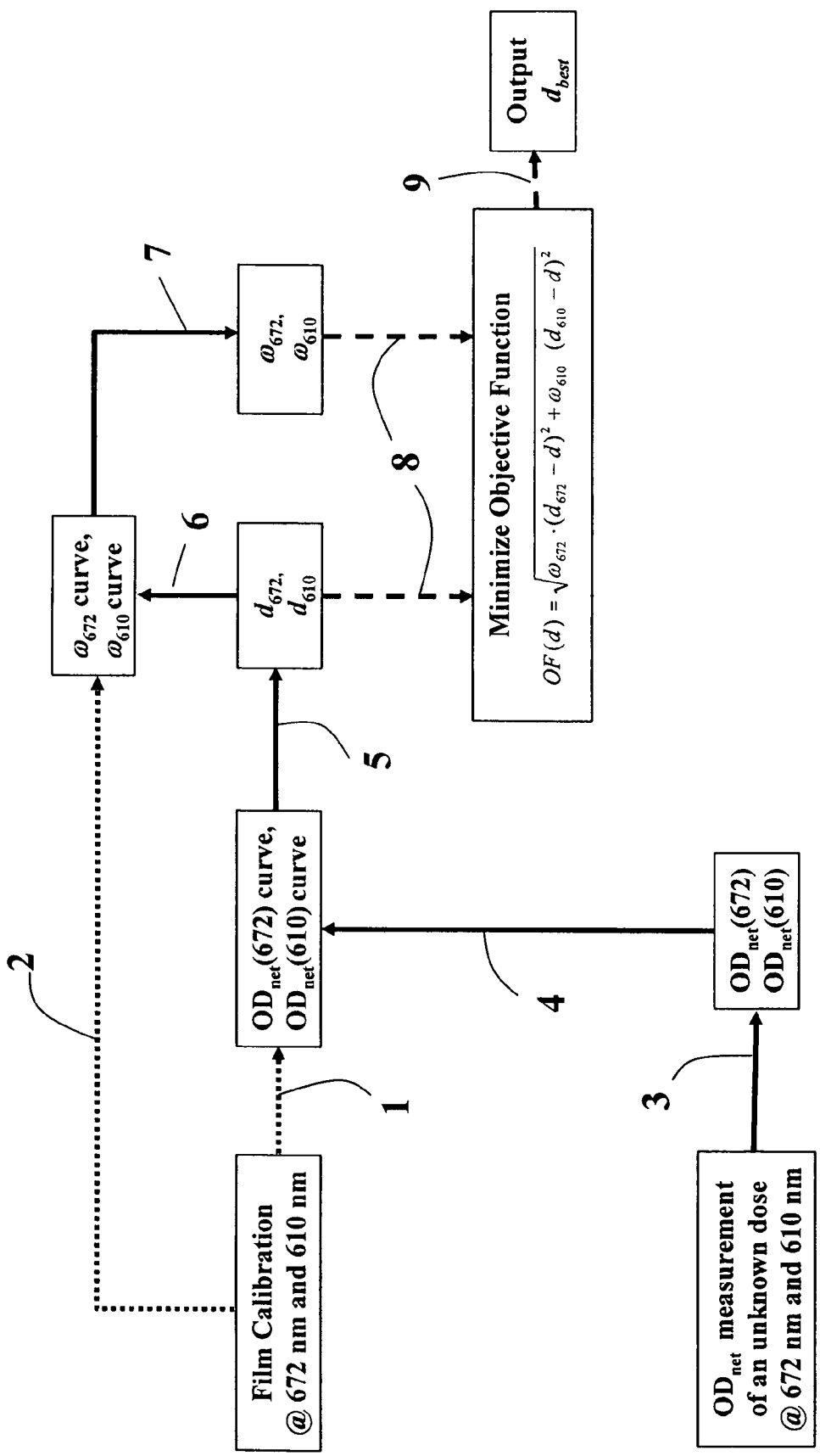
FIG. 2 shows steps of an estimation method according to one embodiment of the invention.

Radiation dose deposited on a radiochromic film can be considered as a dose image. As described above, the dose information recorded on it may be extracted by a proper readout method, preferably in a digital form, and through an appropriate $OD_{net}$-to-dose calibration be converted into a dose matrix with each pixel depicting its corresponding dose value. FIG. 2 is a diagram showing steps in a particular embodiment of the present invention, which uses measurement data at two absorption peaks, 610 and 672 nm, respectively. Step 1 and Step 2 are described in detail in the previous sections. The $OD_{net}$(672) and $OD_{net}$(610) measured (Step 3) for an unknown dose are first converted to doses (steps 4, 5) according to their corresponding film calibration curves. The dose measured at the specific wavelength is denoted by $d_{wavelength}$. The $d_{672}$ and $d_{610}$ thus found are used to determine the weighting factors associated at those dose levels (step 6). Once the corresponding weighting factors, $\omega_{672}$ and $\omega_{610}$, are found (step 7); they are fed together with the $d_{672}$ and $d_{610}$ (step 8) into the weighted objective function in searching for the best estimate ($d_{best}$) of the dose deposited (d) on the RCF through a minimization process (step 9).

The weighted objective function (OF) to be minimized to yield $d_{best}$ is defined to be $$OF(d) = \sqrt{\omega_{672} \cdot (d_{672}-d)^2 + \omega_{610} \cdot (d_{610}-d)^2}, \quad (2)$$

where $\omega_{672}$ and $\omega_{610}$ are used to weigh the terms $(d_{672}-d)^2$ and $(d_{610}-d)^2$ respectively The term $(d_{wavelength}-d)^2$ is the square of the difference of the measured dose at a specific wavelength and the deposited dose; it measures the goodness of fit of d in the OF. The weighting factor, $\omega_{wavelength}$, is actually used to scale the degree of importance of the term $(d_{wavelength}-d)^2$ at different doses and is derived (step 2) from the reciprocal of the uncertainty associated with the measurement made in the film calibration. In an ideal case where the $d_{672}$ and $d_{610}$ give the same value, the OF will be zero for $d_{best}$ equals to $d_{672}$ and $d_{610}$. Minimizing the OF is equivalent to setting its derivative to zero and is easily implemented by software using a local minimizer code written in MatLab code (MathWorks, Inc., Natick, Mass.). The advantage of minimizing the above OF to yield $d_{best}$ is that while searching for d, the accuracy of d with respect to the wavelength used is governed by the weighting factor derived from the measurement uncertainty. In other words, it automatically takes into account the dose magnitude and the associated measurement uncertainty during the minimization process.

MEASUREMENT EXAMPLE

The above described process was applied to estimate doses deposited on a set of nine small film pieces (same batch as used in the film calibration) prepared and irradiated in a set-up similar to the film calibration procedure. The doses given ($D_g$) to the nine film pieces were 5, 13, 24, 27, 37, 40, 50, 60 and 68 Gy. The dose values spanned across the $OD_{net}$ curves with different slopes and were not to coincide with the values used for the film calibration. The readout procedure was the same as described previously. The $OD_{net}$(672) and $OD_{net}$(610) found for each piece were translated into $d_{672}$ and $d_{610}$ using the corresponding film calibration curves. The corresponding $\omega_{672}$ and $\omega_{610}$ were also found from the curves of weighting factors for $d_{672}$ and $d_{610}$, respectively. All the necessary data were then fed into the weighted objective function and the best estimate of d deposited on the film pieces were searched in the minimization process of the objective function. The result yields $d_{best}$ that is the best estimate of the dose deposited on the film piece.

Figure 4:
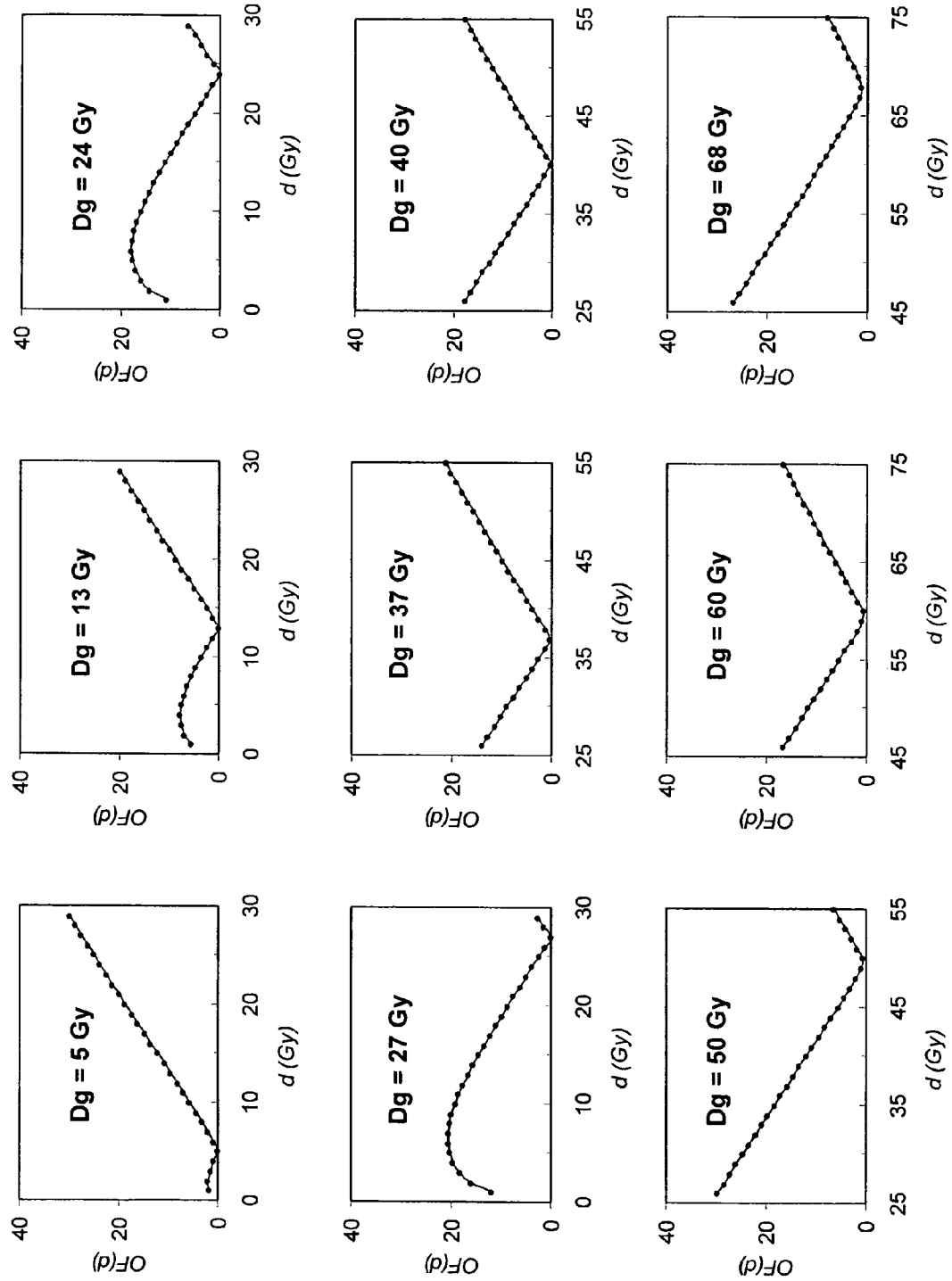
FIG. 4 shows minimization process of objective function for each irradiation dose.

The minimization processes of the objective function for each dose deposited on the film piece are shown graphically in FIG. 4. In each subplot of the figure, the values of the objective function are plotted against a range of dose levels to show how the minimization is achieved by the algorithm. The initial $d_{672}$ and $d_{610}$ found practically form a window within which a solution exists for the minimization. The dose within this window at which the slope of the objective function becomes zero yields the best estimate of the dose, taking into account the uncertainty associated with the measurement. The standard deviation of the individual $OD_{net}$ measurements for the test films at each wavelength did not vary significantly by more than about 3.0%. A quick reference to the objective function might suggest that the uncertainty should be around 4.5% after the error propagation. However, the initial $d_{672}$ and $d_{610}$ form a window within which a solution exists for the minimization, and this feature can literally reduce the total uncertainty to a smaller value because any value of d that lies outside the window is excluded. Therefore, the uncertainty in the dose determination using the objective function is estimated to be less than about ±3%.

Table 1 shows a comparison of the best estimate of the dose ($d_{best}$) with the actual dose deposited ($d_g$) on the film pieces. The best estimate of d was achieved from the minimization of the objective function against the actual dose deposited. There is a good agreement between the given and estimated dose found by the proposed algorithm, the maximum discrepancy being less than 1%. The result shows that the estimation method is robust and efficient, and can be easily implemented with the aid of a spectral microdensitometer, such as the one disclosed in U.S. Pat. No. 6,927,859.

TABLE 1

| Film no. | $d_{best}$ (Gy) | $d_g$ (Gy) | Ratio $\left(\frac{d_{best}}{d_g}\right)$ |
|---|---|---|---|
| 1 | 5.02 ± 0.15 | 5.0 | 1.004 |
| 2 | 13.07 ± 0.39 | 13.0 | 1.005 |
| 3 | 24.04 ± 0.72 | 24.0 | 1.002 |
| 4 | 26.91 ± 0.81 | 27.0 | 0.997 |
| 5 | 37.01 ± 1.11 | 37.0 | 1.000 |
| 6 | 40.04 ± 1.20 | 40.0 | 1.001 |
| 7 | 49.61 ± 1.49 | 50.0 | 0.992 |
| 8 | 59.56 ± 1.79 | 60.0 | 0.993 |
| 9 | 67.85 ± 2.04 | 68.0 | 0.998 |

Implementation of the Method in Devices for Automatic Measurements

The present invention also contemplates implementation of the above described estimation method in a device either as a software module, hardware module or combination of both software and hardware modules for automatic measurements in estimating radiation dose on radiochromic films. Particularly, a spectral microdensitometer, such as the one disclosed in U.S. Pat. No. 6,927,859, may implement and integrate the estimation method for automation so that upon placing the film on the microdensitometer results may be displayed on a screen or printed out. Based on the above disclosure, it is within ordinary skill of people in the art to implement and integrate the estimation method in a device that may be a separate device or a densitometer itself.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method of estimating a radiation dose at a location on a radiochromic film comprising (a) obtaining absorption measurements at two or more wavelengths and (b) minimizing an objective function which takes said absorption measurements or dose values converted from said absorption measurements as input.

2. The method of claim 1, further comprising (c) deriving a curve of weighting factor versus radiation dose at each wavelength at which said absorption measurements are taken in (a).

3. The method of claim 2, wherein said objective function further takes a weighting factor from said curve derived in (c) as input.

4. The method of claim 3, wherein said weighting factor is 1/CoV, wherein CoV=s.d./mean, the s.d.(standard deviation) and the mean being established on a plurality of repeated measurements of a known radiation dose.

5. The method of claim 3, wherein said objective function is:

$$OF(d)=\sqrt{\omega_{w1}\cdot(d_{w1}-d)^2+\omega_{w2}\cdot(d_{w2}-d)^2},$$

wherein $\omega_{w1}$ and $\omega_{w2}$ are weighting factors at doses $d_{w1}$ and $d_{w2}$ for a first wavelength and a second wavelength, respectively; and $d_{w1}$ and $d_{w2}$ are dose values converted from actual net absorption measurements at said first and second wavelengths, respectively.

6. The method of claim 5, wherein said first wavelength is 672 nm and said second wavelength is 610 nm.

7. The method of claim 1, wherein said absorption measurements are obtained at two wavelengths, 672 nm and 610 nm, respectively.

8. The method of claim 1, wherein said dose values are converted from said absorption measurements by using a calibration curve.

9. The method of claim 8, wherein said calibration curve is obtained by plotting $OD_{net}$ as a function of known doses for each wavelength and then using a polynomial curve fitting technique; said $OD_{net}$ being net optical density.

10. The method of claim 1, wherein said objective function is:

$$OF(d)=\sqrt{\omega_{w1}\cdot(d_{w1}-d)^2+\omega_{w2}\cdot(d_{w2}-d)^2},$$

wherein $\omega_{w1}$ and $\omega_{w2}$ are weighting factors at doses $d_{w1}$ and $d_{w2}$ for a first wavelength and a second wavelength, respectively; and $d_{w1}$ and $d_{w2}$ are dose values converted from actual net absorption measurements at said first and second wavelengths, respectively.

11. The method of claim 10, wherein said first wavelength is 672 nm and said second wavelength is 610 nm.

12. A device for estimating a radiation dose at a location on a radiochromic film, comprising a component for minimizing the following objective function:

$$OF(d)=\sqrt{\omega_{w1}\cdot(d_{w1}-d)^2+\omega_{w2}\cdot(d_{w2}-d)^2},$$

wherein $\omega_{w1}$ and $\omega_{w2}$ are weighting factors at doses $d_{w1}$ and $d_{w2}$ for a first wavelength and a second wavelength, respectively; and $d_{w1}$ and $d_{w2}$ are dose values converted from actual net absorption measurements at said first and second wavelengths, respectively.

13. The device of claim 12, wherein said first wavelength is 672 nm and said second wavelength is 610 nm.

14. The device of claim 13, further comprising a component for measuring optical density of a radiochromic film at a given wavelength.

15. The device of claim 14, further comprising a component for deriving a curve of weighting factor versus radiation dose.

16. The device of claim 15, further comprising a component for converting an optical density into a dose value.

17. The method of claim 1, wherein said objective function further takes as input a weighting factor for each of said absorption measurements or said dose values.

18. The method of claim 17, wherein each of said weighting factors is 1/CoV for its corresponding absorption measurement or dose value.

* * * * *